United States Patent [19]
Johnson et al.

[11] Patent Number: 5,989,216
[45] Date of Patent: Nov. 23, 1999

[54] ACCESS PORTAL AND METHOD

[75] Inventors: Theodore A. Johnson, St. Paul; Harry A. Puryear, Shoreview, both of Minn.

[73] Assignee: SIMS Deltec, Inc., St. Paul, Minn.

[21] Appl. No.: 08/670,006

[22] Filed: Jun. 25, 1996

Related U.S. Application Data

[60] Provisional application No. 60/000,644, Jun. 29, 1995.

[51] Int. Cl.$^6$ .................................................. A61M 11/00
[52] U.S. Cl. ............................ 604/93; 604/175; 604/256; 604/905
[58] Field of Search ............................. 604/93, 256, 175, 604/905

[56] References Cited

U.S. PATENT DOCUMENTS

| | | |
|---|---|---|
| 3,898,988 | 8/1975 | Morgan . |
| 4,452,473 | 6/1984 | Ruschke . |
| 4,557,722 | 12/1985 | Harris . |
| 4,588,394 | 5/1986 | Schulte et al. . |
| 4,592,749 | 6/1986 | Ebling et al. . |
| 4,655,765 | 4/1987 | Swift . |
| 4,665,959 | 5/1987 | Takagi . |
| 4,673,394 | 6/1987 | Fenton, Jr. et al. . |
| 4,675,007 | 6/1987 | Terry . |
| 4,704,103 | 11/1987 | Stober et al. . |
| 4,710,174 | 12/1987 | Moden et al. . |
| 4,723,948 | 2/1988 | Clark et al. . |
| 4,738,657 | 4/1988 | Hancock et al. . |
| 4,767,410 | 8/1988 | Moden et al. . |
| 4,772,270 | 9/1988 | Wiita et al. . |
| 4,772,276 | 9/1988 | Wiita et al. . |
| 4,778,452 | 10/1988 | Moden et al. . |
| 4,781,680 | 11/1988 | Redmond et al. . |
| 4,781,685 | 11/1988 | Lehmann et al. . |
| 4,802,885 | 2/1989 | Weeks et al. . |
| 4,836,873 | 6/1989 | Landskron et al. . |
| 4,838,887 | 6/1989 | Idriss . |
| 4,840,615 | 6/1989 | Hancock et al. . |
| 4,861,341 | 8/1989 | Woodburn . |
| 4,871,351 | 10/1989 | Feingold . |
| 4,880,414 | 11/1989 | Whipple . |
| 4,892,518 | 1/1990 | Cupp et al. . |
| 4,904,241 | 2/1990 | Bark . |
| 4,915,690 | 4/1990 | Cone et al. . |
| 4,929,236 | 5/1990 | Sampson . |
| 4,963,133 | 10/1990 | Whipple . |
| 4,978,338 | 12/1990 | Melsky et al. . |
| 4,994,048 | 2/1991 | Metzger . |
| 5,006,115 | 4/1991 | McDonald . |
| 5,013,298 | 5/1991 | Moden et al. . |
| 5,026,344 | 6/1991 | Dijkstra et al. . |
| 5,041,098 | 8/1991 | Loiterman et al. . |
| 5,045,060 | 9/1991 | Melsky et al. . |
| 5,085,644 | 2/1992 | Watson et al. . |
| 5,090,954 | 2/1992 | Geary . |
| 5,092,849 | 3/1992 | Sampson . |
| 5,108,377 | 4/1992 | Cone et al. . |
| 5,129,891 | 7/1992 | Young . |
| 5,137,529 | 8/1992 | Watson et al. . |
| 5,147,483 | 9/1992 | Melsky et al. . |
| 5,149,330 | 9/1992 | Brightbill . |
| 5,167,638 | 12/1992 | Felix et al. . |
| 5,171,228 | 12/1992 | McDonald . |
| 5,178,612 | 1/1993 | Fenton, Jr. . |
| 5,180,365 | 1/1993 | Ensminger et al. . |
| 5,185,003 | 2/1993 | Brethauer . |
| 5,213,574 | 5/1993 | Tucker . |
| 5,281,199 | 1/1994 | Ensminger et al. . |
| 5,312,337 | 5/1994 | Flaherty et al. . |
| 5,318,545 | 6/1994 | Tucker . |
| 5,336,194 | 8/1994 | Polaschegg et al. . |
| 5,360,407 | 11/1994 | Leonard . |
| 5,387,192 | 2/1995 | Glantz et al. . |
| 5,558,641 | 9/1996 | Glantz et al. . |

FOREIGN PATENT DOCUMENTS

| | | |
|---|---|---|
| 0 258 777 | 3/1988 | European Pat. Off. . |
| 59880 | 8/1954 | France . |
| 3528878 | 2/1987 | Germany . |
| 2191701 | 12/1987 | United Kingdom . |
| 9014118 | 11/1990 | WIPO . |

OTHER PUBLICATIONS

Exhibit 1 (11 pgs.) "DAVOL Implanted Ports with Groshong™ Catheter—Use and Maintenance," Bard Access Systems, Salt Lake City, UT; Feb. 1992.

Exhibit 2 (14 pgs.) "Implanted Ports with Hickman® Catheter—Use and Maintenance," Bard Access Systems, Salt Lake City, UT; Feb. 1992.

Exhibit 3 (1 pg.) Photograph: CELSA product.

Exhibit 4 (4 pgs.) "Chemo–Port® Implantable Vascular Access Ports," HDC Corporation, San Jose, CA; 1991.

Exhibit 5 (3 pgs.) "TrimPort™ Series Superior Vascular Access," Gerard Medical, Inc., Massachusetts; undated.

Exhibit 6 (3 pgs.) "For secure fluid delivery to vascular access ports," Gish Biomedical, Inc., Irvine, CA; Mar.–Apr. 1993.

Exhibit 7 (2 pgs.) "A–Port™ Implantable Vascular Access Sysetm," Therex Corporation, Walpole, MA; 1992.

Exhibit 8 (8 pgs.) "Vascular Access Products," Strato Medical Corporation/Pfizer, Beverly, MA; Sep. 1991.

Exhibit 9 (1 pg.) "NORPORT™–LS Vascular–Access Port," Norfolk Medical, Skokie, IL; undated.

Exhibit 10 (1 pg.) "OMEGAPORT™ Implantable Access System for All Therapies," Norfolk Medical, Skokie, IL; Jan. 1, 1992.

Exhibit 11 (2 pgs.) "SURE CATH® Port Access Catheter," Ivion Corporation, Broomfield, CO; 1992.

Exhibit 12 (4 pgs.) "Access Ability—the S.E.A.-Port® Topsider™," Harbor Medical Devices, Inc., Jaffrey, NH; 1991.

Exhibit 13 (5 pgs.) "Turning Vascular Access on its Side—S.E.A.-Port™," Harbor Medical Devices, Inc., Jaffrey, NH; undated.

Exhibit 14 (4 pgs.) "Covering the Angles on Access," Harbor Medical Devices, Inc., Jaffrey, NH; 1989.

Exhibit 15 (4 pgs.) "The Key to a Good Vascular Access Port System is Using the Right Combination," Gish Biomedical, Inc., Irvine, CA; 1987.

Exhibit 16 (2 pgs.) "ImPort™—Vascular Access Port," Pudenz–Schulte Medical Corporation, Goleta, CA; undated.

Exhibit 17 (2 pgs.) "Functionally Superior," Therex Corporation, Walpole, MA; 1992.

Exhibit 18 (2 pgs.) "Dimensionally Distinctive," Therex Corporation, Walpole, MA; undated.

Exhibit 19 (4 pgs.) "Oncology/Critical Care," Quinton Instrument Company (an A. H. Robins Company), Seattle, WA; Jul. 1988.

*Primary Examiner*—Mark Bockelman
*Attorney, Agent, or Firm*—Merchant & Gould P.C.

[57] ABSTRACT

The present invention provides a portal for subcutaneous implantation, where the portal includes a housing having a first end, a second end, an inner wall, and a lumen between the first and second open ends. In one preferred embodiment, the first open end of the housing is sealed by a elastomeric septum, which has been injection molding into place. The elastomeric septum is bonded to the inner wall of the housing adjacent the first open end. The second open end is sealed to define a reservoir accessible through the septum.

36 Claims, 8 Drawing Sheets

ACCESS PORTAL AND METHOD

CROSS-REFERENCE TO RELATED APPLICATIONS

This application claims priority under 35 U.S.C. §119(e) to U.S. Provisional Application No. 60/000,644 filed on Jun. 29, 1995.

TECHNICAL FIELD

The present invention relates to implantable biocompatible access portals used in connection with the delivery of medicants, and other pharmaceutical fluids into a body, or the withdrawal of fluids from the body.

BACKGROUND

Access portals provide a convenient method to repeatedly deliver medicants to remote areas of the body without utilizing surgical procedures. Portals are totally implantable within the body, i.e. subcutaneous, and permit the infusion of medicants, parenteral solutions, blood products, and other fluids. Portals may also be used for blood sampling.

A typical portal generally includes a housing assembly, a septum, and an outlet. The housing assembly and septum define a reservoir which is accessible through the septum. The outlet includes or is attached to a catheter which accesses a vein. The catheter delivers fluid from the portal to a remote location in the body, for example the superior vena cava. The outlet may be an integral catheter as in U.S. Pat. No. 4,471,885 to Weeks, or a separate metallic outlet tube assembly as in U.S. Pat. No. 5,213,574 to Tucker. In the case of a portal with an outlet tube assembly, a catheter will be attached thereto.

In common practice, the portal is implanted within the body and the catheter is routed to a remote area were fluid is desired to be delivered. To deliver the fluid, a caregiver locates the septum of the portal by palpation of the patient's skin. Portal access is accomplished by percutaneously inserting a needle, typically a non-coring needle, perpendicularly through the septum of the portal and into the reservoir. The drug or medicant is then administered by bolus injection or continuous infusion. Ordinarily, the fluid flows through the reservoir into the catheter and finally to the site were the fluid is desired.

Portals generally come in two different types, surgical and cosmetic. Surgical portals are used to deliver medicants, including chemotherapy drugs which may be harmful to surrounding tissue, as well as sampling blood. Cosmetic portals, on the other hand, are utilized to deliver saline or some other non-reactive substance to a prosthesis which supplements a body feature. An example of a surgical portal is shown in U.S. Pat. No. 5,213,574, while an example of a cosmetic portal is shown in U.S. Pat. No. 4,471,885.

A concern for all portals, and especially portals used for surgical procedures, is blowout. Blowout describes the catastrophic failure of a portal when the pressure inside the reservoir is great enough to disengage the septum from the housing of the portal. Disengagement of the septum may injure the patient, and release medication contained in the portal. The released medicant will often be harmful to the surrounding tissue. Blowouts have a variety of causes. For example, a blowout may be caused if the catheter downstream of the portal is occluded and a bolus injection is attempted. When the bolus injection is attempted the injected fluid cannot travel through the catheter and as fluid is continually injected into the reservoir of the portal the pressure increases until the septum is disengaged.

Blowouts are of a much greater concern for surgical portals than for cosmetic portals. A primary reason for this is that the reservoirs of surgical portals often contain caustic medicants while the reservoirs of cosmetic portals do not. To prevent blowout, surgical portals typically hold the septum in the housing of the portal under great compression. For example, the SIMS Deltec PORT-A-CATH brand portal uses an interference fit to both radially and axially compress the septum to hold it in place.

In contrast, some cosmetic portals, for example, the portal shown in U.S. Pat. No. 4,371,885, are sealed to the housing by compressing only a preformed ridge around the septum with, for example, a threaded ring. The threaded ring of U.S. Pat. No. 4,371,885 does not provide as much compressive force as the PORT-A-CATH portal.

Another concern with portals, and more importantly with surgical portals, is puncture life. Puncture life describes the number of punctures a septum can resist and still provide a fluid tight seal. If the septum does not reseal after an injection is made, the injected medicant may leak out of the reservoir and possibly harm the surrounding tissue. Once again, septum life is of greater importance in surgical portals than cosmetic portals because of the nature of the medicant being injected. Commercially successful prior art surgical portals have also utilized a compressed septum to increase puncture life.

Typical portals are manufactured with preformed or discrete septums. The portal is assembled by inserting the septum into the housing and then compressing the septum. The septum can be compressed either with separate components or by "shoehorning" a larger septum into a housing having an aperture with a smaller diameter. An example of a portal with a "shoehorned" septum is shown in U.S. Pat. No. 5,045,060 to Melsky et al. A disadvantage of any portal having a preformed septum is increased cost of manufacture. The increased cost is caused, in part, by the fact that the components used to seal the septum require precise tolerances in their dimensions.

Another concern with preformed septums compressively sealed against the portal is a decrease in the target area, provided by the septum, to the caregiver. The target area describes the exposed portion of the septum, through which a needle can access the reservoir. Some prior art portals have attempted to increase the "target area" of the septum available to the caregiver without much success. For example, some of these prior art devices have attempted to increase the target area by providing integrally molded elastomeric domes accessible from a plurality of directions. However, the integrally molded domes of the prior art have at least two significant problems. The first problem is that the caregiver is never completely sure when the needle is in the reservoir. For example, the caregiver may push the needle through a side wall and out into the body cavity, believing the needle to be in the reservoir. Second, when pushing the needle into the reservoir the elastomeric dome may collapse, thereby inhibiting injection of any medicant into the reservoir.

Solutions to the problems with domed portals have been proposed by the prior art. An example is an OMEGAPORT brand portal manufactured by Norfolk Medical of Skokie, Ill. The OMEGAPORT brand portal includes an elastomeric dome which is reinforced by an internal wire cage. The wire cage solves the problem of the dome collapsing upon insertion of the needle, but provides no indication to the caregiver of when the needle is in the reservoir. Further, the wire cage presents its own problems. These problems include needles deflecting off of the cage and away from the reservoir.

Therefore, a need has arisen to provide a portal and a method of manufacture which effectively increases the target area of the portal, yet achieves all of the benefits of traditional portals which utilize compressed septums. Additionally there is a need to decrease the cost of manufacturing portals, including making portals easier to manufacture. The portal of the present invention solves these and other problems of the prior art.

SUMMARY OF THE INVENTION

The invention includes an implantable portal having a housing and a septum. The housing includes a lumen accessible through a first open end, and the lumen includes an inner wall. The septum has an outer periphery bonded to the inner wall adjacent the first open end of the housing.

Preferably, the housing further includes an outlet tube assembly operative in accessing the lumen.

Preferably, the septum is injection molded into the lumen of the housing.

In one implementation, the inner wall of the housing includes a roughened surface. In other implementations, the inner wall of the housing includes a groove. The inner wall of the housing may include an adhesion promoter thereon.

Preferably, the housing further includes a second open end opposite from the first open end; the second open end includes an associated diameter; and the portal further comprises a seal operative to close the second open end of the housing. The seal may include a cup-shaped insert. The cup-shaped insert may be ultrasonically staked to the housing.

Preferably, the septum includes a flanged region, and the cup-shaped insert squeezably engages the flanged region. The septum includes a bottom surface facing the lumen, and the bottom surface may be undulated in shape.

In another aspect, the invention includes a method of assembling a portal comprising the steps of providing a housing having a first open end; and injection molding an elastomeric septum in the first open end of the housing.

Preferably, the method further comprises the step of sealing the second end to form a fluid tight reservoir accessible through the injection molded septum. The second open end may be sealed with a cup-shaped insert.

Preferably, the method further includes the step of ultrasonically staking the housing to the cup-shaped insert.

The method may include the step of forcing the cup-shaped insert into the second open end of the housing to provide an interference fit.

In another aspect, the invention includes a portal comprising a septum, an insert, and a housing. The septum includes first and second opposite surfaces, the second surface being undulated. The insert engages the septum. The housing holds the septum and the insert.

Preferably, the septum includes a flanged region, and the insert forceably squeezes the flanged region.

In one implementation, the septum is injection molded into the housing. In another implementation, the septum is shoe-horned into the housing.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE ILLUSTRATED EMBODIMENTS

The portal of the present invention includes a septum which is non-compressively held in a housing of a portal. As used herein and as known in the art, the term "non-compressively held" means not gripped by compressing across the entire vertical dimension of the septum. That is, a "compressively held" septum is one which is gripped and squeezed across the entire vertical dimension. The present invention includes a septum which is not squeezed across its entire vertical dimension. In the first preferred method of the present invention, the septum is injection molded into the housing. It has been found that non-compressively held septums provide an increased septum puncture life as compared to compressed septums. Further, it has been found that an injection molded septum resists "blowout" as well or even better than the compressed septums of the prior art. The housing may be sealed in a variety of fashions as to define a sealed reservoir.

In reference to the drawings, in which like elements are numbered alike in the various figures, the methods and embodiments of the unique portal method of manufacture and portal are shown.

Figure 1:
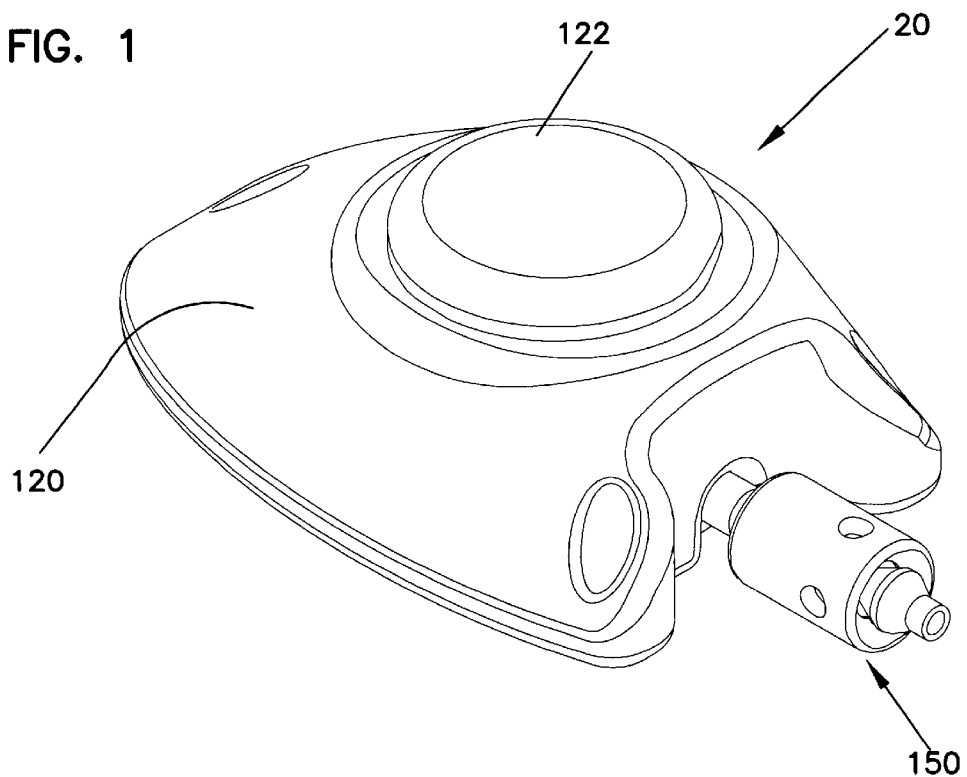
FIG. 1 is a perspective view of a portal, embodying the present invention.

FIG. 1 is a perspective view of an implantable biocompatable access portal 20. Portal 20 is totally implantable within the human body, and permits the infusion of medicants, parenteral solutions, blood products, and other fluids. Portal 20 includes a housing 120 and a septum 122 for receiving a needle. An outlet tube assembly 150 communicates with a hollow inner portion of portal 20, which will be explained below. Outlet tube assembly 150 may be connected with a catheter in order to deliver medical fluids or the like through a vein in the body.

Figure 2:
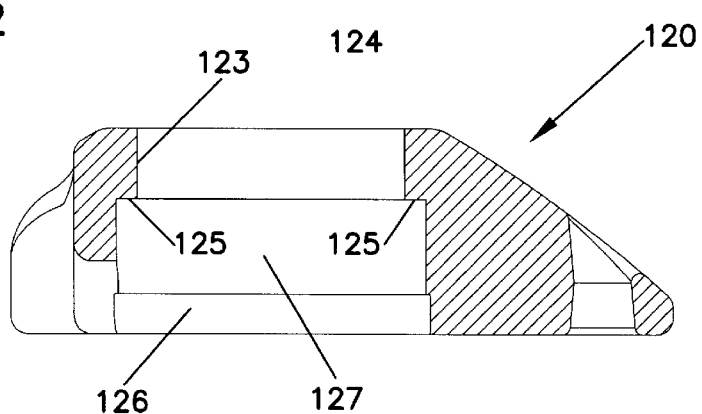
FIG. 2 is a cross-sectional view of a housing, embodying the present invention.

FIG. 2 illustrates a cross-section of portal housing 120. Portal housing 120 includes a first open end 124 and a second open end 126 having a lumen 127 therebetween. Housing 120 includes an inner wall 123 positioned between first open end 124 and second open end 126. Preferably inner wall 123 has an associated flange 125 portioned between first open end 124 and second open end 126. In a first preferred embodiment, both first open end 124 and second open end 126 are circular and include associated diameters.

Figure 3:
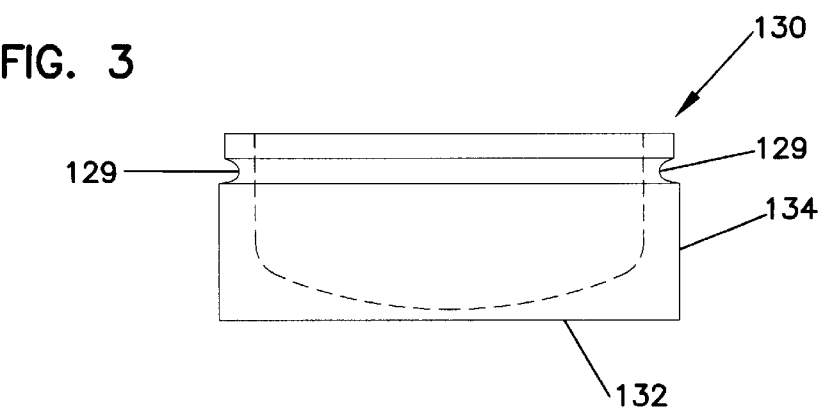
FIG. 3 is a side plan view of a cup-shaped insert, embodying the present invention.

A cup-shaped insert 130 is illustrated in FIG. 3. Cup-shaped insert 130 is for engaging second open end 126 of portal housing 120. Cup-shaped insert 130 is preferably constructed from metal, such as titanium or stainless steel. Insert 130 includes a bottom 132 and a continuous sidewall 134. Sidewall 134 includes an associated diameter which may be slightly greater than the inner diameter of lumen 127 of housing 120. Sidewall 134 includes an associated height. Insert 130 also includes an annular groove 129 positioned on sidewall 134. The various purposes for groove 129 will be explained in more detail below. Shown in phantom is an inner surface 25 of insert 130. Inner surface 25 is for holding the medicant or whatever fluid is being delivered through septum 122 into lumen 127, into tube assembly 150, and ultimately into the patient's body. An outlet 78 extends from sidewall 134 to inner surface 25 to accommodate passage of outlet tube assembly 150.

Figure 4:
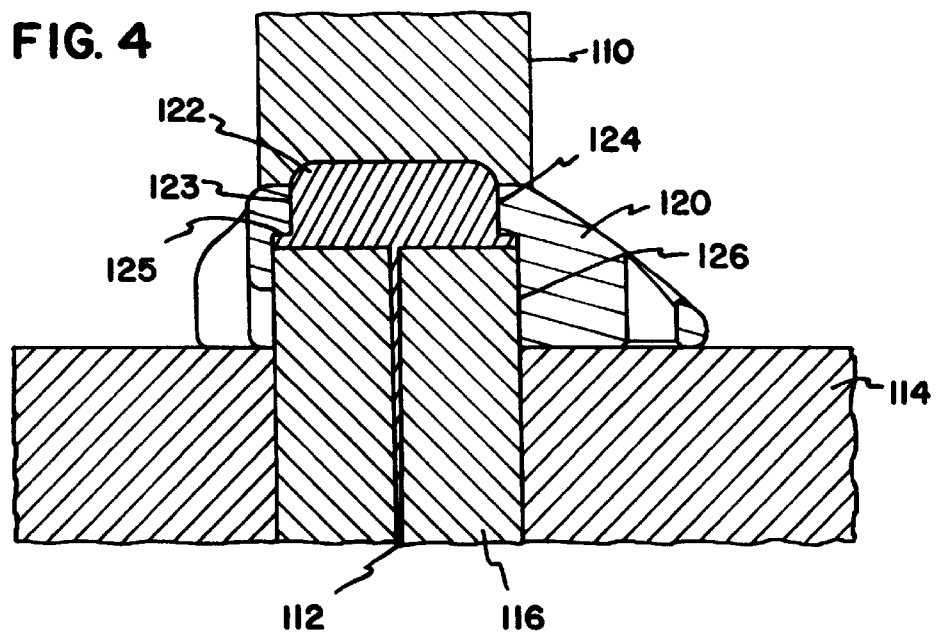
FIG. 4 is a cross-sectional plan view of a partially assembled portal positioned in an injection molding fixture according to one preferred method of manufacture.

As shown in FIG. 4, septum 122 is injection molded into first open end 124 of housing 120. The injection molding process is described in greater detail below. Septum 122 is positioned against inner wall 123 adjacent first open end 124. Septum 122 is held into housing because of chemical and mechanical bonding forces. More exactly, it is the outer periphery of septum 122 which interacts with housing 120 to bond septum 122 into first open end 124 of housing 120. The chemical forces are created by adhesives, while the mechanical forces are created by surface irregularities. While the exact chemical forces are not known, these forces are believed to possibly include one or more of the following: covalent bonding; pseudo bonding; hydrogen bonding; steric interaction, and; molecular intermingling. The mechanical forces describe obstructions to removal of the septum, such as grooves or a roughened surface, which prevent the smooth removal of the septum. For example, in the preferred embodiment, septum 122 covers flange 125. By covering flange 125, septum 122 is mechanically held into housing 120.

Figure 6:
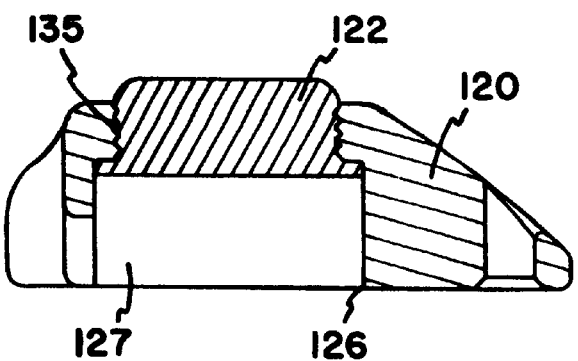
FIG. 6 is a cross-sectional plan view of a portal including threads adjacent a septum according to another preferred embodiment.

Inner wall 123 of housing 120, which contacts septum 122, may be mechanically altered to create additional connection forces between septum 122 and inner wall 123. For example, and as stated previously, that portion of the inner wall 123 in contact with septum 122 may include a roughened surface which improves mechanical adhesion between septum 122 and housing 120. The roughened surface may be created by sand or shot blasting, sanding, chemical etching, or the equivalent. The improved mechanical connection may also be created by providing an annular groove 135 in inner wall 123, or a series of annular grooves 135 in inner wall 123 as best shown in FIG. 6. The mechanical techniques increase adhesion because there is more surface contact between septum 122 and inner wall 123. Further, the uneven surface created by the above increases the "grip" of the injected molded septum on the housing, which improves axial adhesion.

The adhesion between inner wall 123 and septum 122 is created by treating the inner wall 123 of housing 122 with an adhesion promoter. An example of an acceptable adhesion promoter is sold under the trademark CHEM-LOK 608, by Lord Elastomer Products, located in Erie, Pa. The active ingredient in CHEM-LOK 608 adhesion promoter is silane. This adhesion promoter works equally well with both metallic and non-metallic housings. The adhesion promoter creates a chemical bond between the elastomeric and itself.

Figure 5:
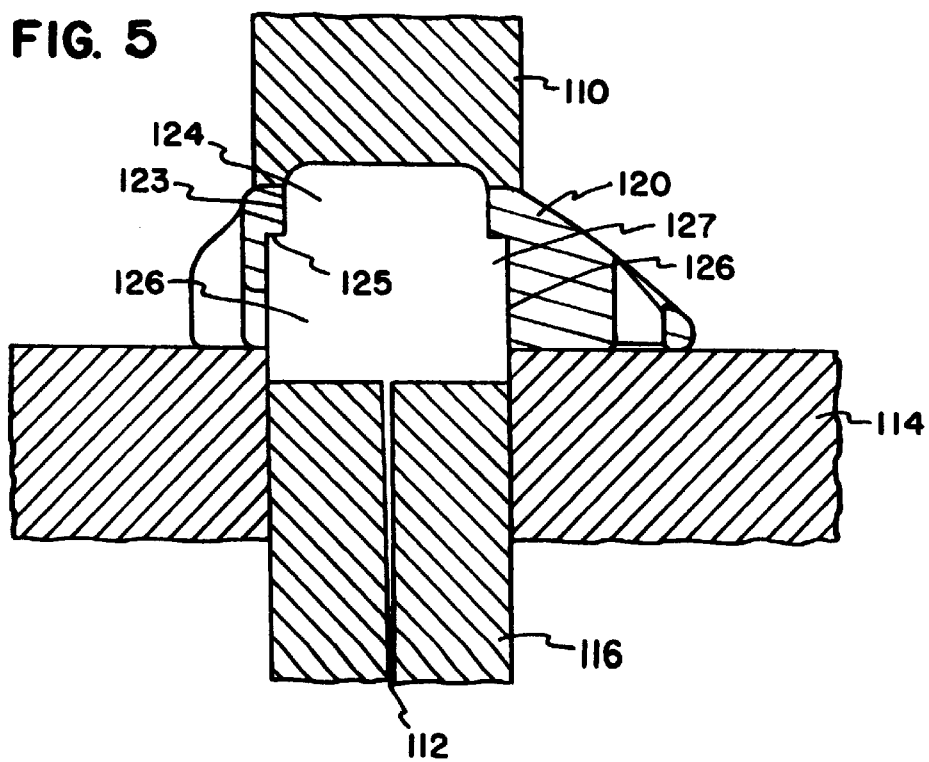
FIG. 5 is a cross-sectional plan view of the partially assembled portal of FIG. 1 prior to injection molding.
Figure 7:
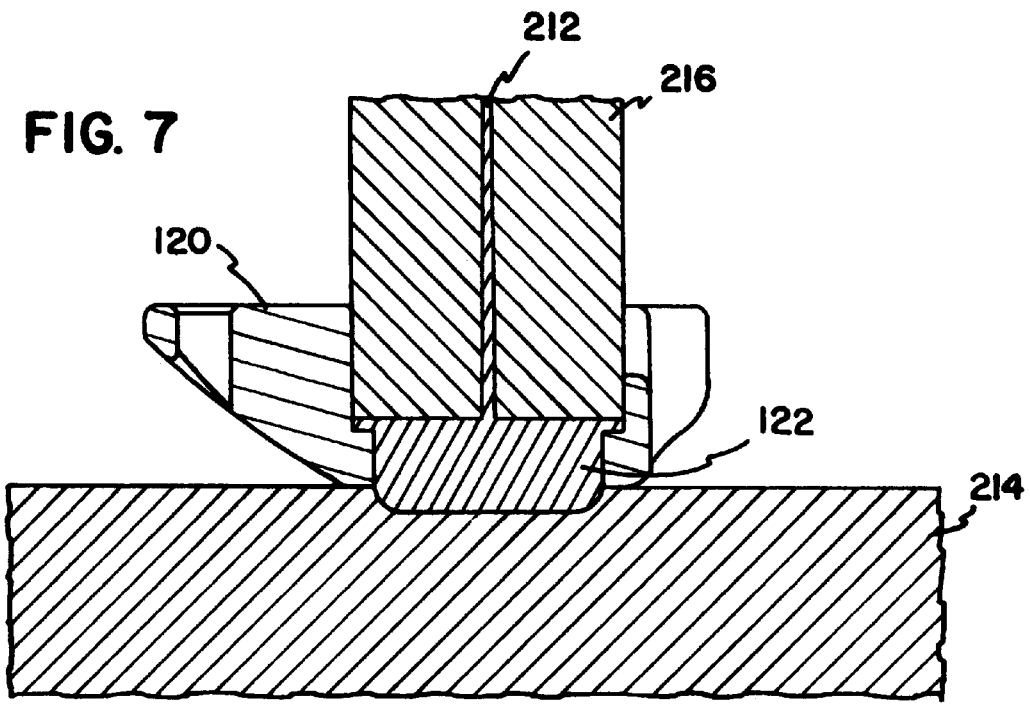
FIG. 7 is a cross-sectional plan view of a partially assembled portal in an injection molding fixture according to another preferred method of manufacture.

Septum 122 may be injection molded in a variety of fashions, as best illustrated in FIGS. 4, 5 and 7. As illustrated in FIGS. 4 and 5, housing 120 is placed on fixture 114 so that second open end 126 of housing 120 is positioned on a core pin 116. Core pin 116 extends through fixture base 114 into lumen 127 of housing 120, and includes a passage 112 operative in delivering an elastomeric material which will form septum 122. An example of a suitable elastomeric material is silicone. An upper mold piece 110 engages housing 120 proximate first open end 124 to define an upper surface of septum 122. In the injection molding process, the elastomeric material may flow out beyond upper mold piece 110. This will cause a flash which may be trimmed later in the process.

With continued reference to FIG. 5, upper mold piece 110 defines the outer features of septum 122, while core pin 116 defines the inner features of septum 122. Passage 112 could be positioned on either upper mold 110 or core pin 116, however, positioning passage 112 in core pin 116 is preferred so that the outer surface of septum 122 does not include any gate vestige. Gate vestige describes an excess of elastomeric material which is deposited adjacent passage 112. After injection, the elastomeric material will cure to provide a pierceable septum. Elastomeric materials other than silicone may also be used to construct the septum.

After the elastomeric material has cured, upper mold piece 110 of FIGS. 4 and 5 may be removed and housing 120 and septum 122 may be disengaged from fixture 114 and core pin 116. Any flash may then be trimmed. The portion of lumen 127 of housing 120 adjacent core pin 116 will define a reservoir 140 operable to receive liquid pharmaceuticals, or medicants. Second open end 126 of housing 120 may be sealed in a variety of fashions as will be described in greater detail hereinafter.

A second preferred method of injection molding the septum of a portal is illustrated in FIG. 7. The second preferred method also provides a technique to injection mold a septum into a housing. The second preferred method eliminates the need for upper mold piece 110. Specifically, a lower mold 214 is provided which defines the outer characteristics of septum 122, while a core pin 216 delivers the elastomeric material through a passage 212.

In either of the injection molding methods illustrated in FIGS. 4 and 5 or FIG. 7, the elastomeric material can be injected through core pin 116 or upper mold piece 110 as shown in FIG. 4, or core pin 216 or lower mold 214 as in FIG. 7. However, in either embodiment, it is preferred to inject from the reservoir side of the septum. This is preferred because any gate vestige will not be readily apparent to the user.

Figure 8:
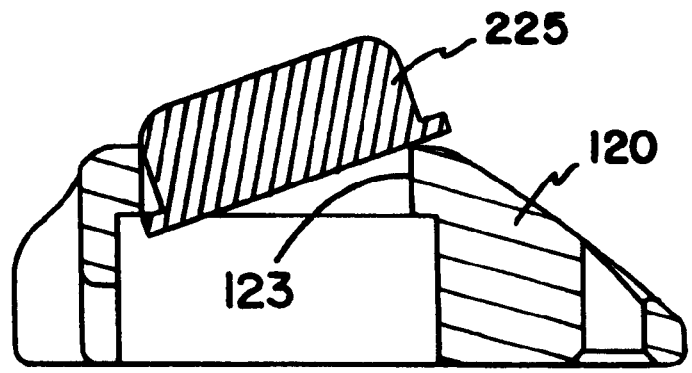
FIG. 8 is a cross-sectional plan view of a partially assembled portal, with a septum partially placed therein, according to another preferred method of manufacture.
Figure 9:
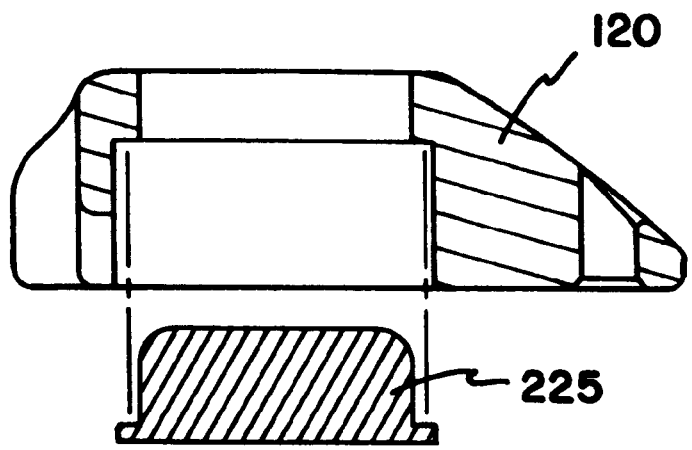
FIG. 9 is a cross-sectional plan view of a partially assembled portal, with a septum partially placed therein, according to another preferred method of manufacture.

Injection molding is one method of manufacturing a portal according to the present invention. Other techniques or methods are also contemplated. For example, as shown in FIGS. 8 and 9, a septum may be held in the first open end of the housing only by an adhesion promoter. FIGS. 8 and 9 illustrate a preformed septum 225 having outer dimensions the same as or smaller than first open end 124. Inner wall 123 is treated with an adhesion promoter, such as CHEM-LOK 608 and then septum 225 may be shoehorned in as shown in FIG. 8 or dropped in as shown in FIG. 9. Septum 225 will then be bonded to housing 120 with the adhesion promoter only and not through any compressive forces on septum 225. The injection molding process in addition to the methods shown in FIGS. 8 and 9 are considered to be non-compressive because neither housing 120, nor any other components, exert forces across the entire vertical dimension of the septum to seal it in the open end of the housing. An example of a compressively held septum is shown in U.S. Pat. No. 5,387,192, to Glantz et al., the specification and drawings of which are herein incorporated by reference.

After septum 122 has been injected molded, or otherwise inserted into first open end 124 of housing 120, second open end 126 is sealed to define a reservoir 140 accessible through septum 122. FIGS. 10–14 illustrate different ways in which second open end 126 of housing 120 may be sealed. These examples are not intended to be limiting, but rather only exemplify a few the many possible techniques available to seal second open end 126 of housing 120.

Figure 10:
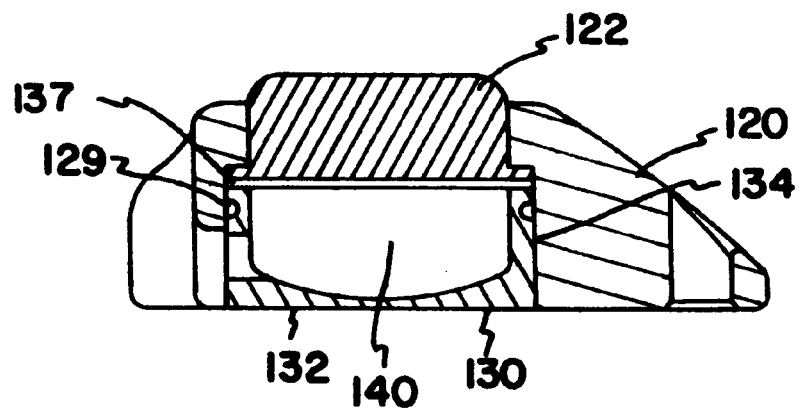
FIG. 10 is a cross-sectional plan view of a sealed portal according to another preferred embodiment.
Figure 11:
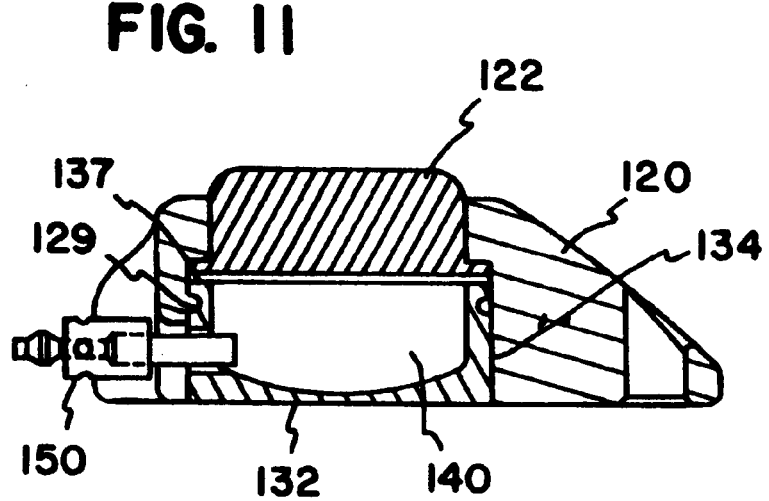
FIG. 11 is the portal of FIG. 10 including an outlet tube assembly.

With reference to FIGS. 10 and 11 there is shown housing 120 with septum 122. In this specific embodiment, housing 120 of the portal as shown in FIGS. 10 and 11 is of a non-metallic, plastic construction, such as polysulfone. Second open end 126 is shown engaging cup-shaped insert 130. In this particular embodiment, the associated height of cup-shaped insert 130 is not great enough to contact septum 122 when bottom 132 of cup-shaped insert 130 is flush with the bottom of the housing 120. That is, a gap 137 exists between cup-shaped insert 130 and septum 122.

The portal of FIGS. 10 and 11 is assembled by ultrasonically staking metallic cup-shaped insert 130 to non-metallic housing 120. Specifically, cup-shaped insert 130 is ultrasonically vibrated and simultaneously forced into the lumen of housing 120. Vibrating cup-shaped insert 130 melts the plastic of housing 120 as it is forced therein. The melted plastic is pushed, by cup-shaped insert 130 into an annular groove 129 positioned on side wall 134 of cup-shaped insert. Further, the plastic from housing 120 is pushed into gap 137 between cup-shaped insert 130 and septum 122. Cup-shaped insert 130 is no longer pushed into lumen 127 of housing 120 when bottom 132 of cup-shaped insert 130 is flush with the bottom of housing 120.

FIG. 11 illustrates the portal of FIG. 10 with outlet tube assembly 150. Outlet tube assembly 150 may be of any type including, but not limited to, that illustrated in FIG. 11. The outlet tube assembly of FIG. 11 could be used with any of the portals illustrated in FIGS. 12–14.

Figure 12:
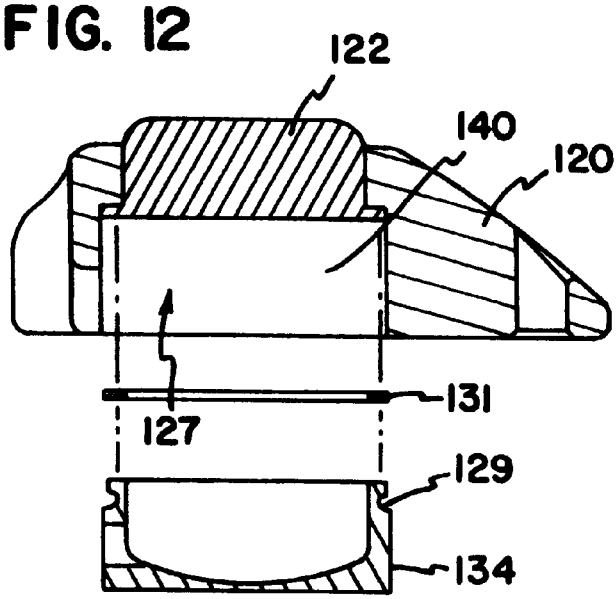
FIG. 12 is a cross-sectional exploded plan view of a partially assembled portal according to another preferred embodiment.

FIG. 12 illustrates a second embodiment of sealing second open end 126 of housing 120. In particular, cup-shaped 130 insert includes two diameters, a diameter smaller than the diameter of second open end 126 above groove 129 and a diameter larger than the diameter of second open end 126 below groove 129. In this particular arrangement, the height of wall 134 is not great enough to contact septum 122. The smaller diameter above annular groove 129 helps to center cup-shaped insert 130 in lumen 127 of housing 120. A non-metallic ring 131, preferably constructed from plastic such as polysulfone is also included. Ring 131 is positioned between the upper rim of cup-shaped insert 130 and septum 122. Cup-shaped insert 130 is ultrasonically staked into housing such that housing 120 is melted into annular groove 129. As cup-shaped insert 130 is forced into lumen 127 of housing 120, ring 131 is pushed into contact with septum 122. Ring 131 does not exert compression across the entire vertical dimension of the septum. As such, septum 122 is non-compressively held in housing 120.

While the ultrasonic staking technique illustrated in FIGS. 10–12 is preferred, cup-shaped insert 130 may be bonded to housing 120 in a variety of other ways as well. These ways include mechanical and chemical techniques. For example, in the case of an all metal housing, an all metal cup-shaped insert may engage second open end and seal housing 120 through an interference fit. Specifically, the cup-shaped insert would include an outer diameter slightly larger than the diameter of second open end 126, and the cup-shaped insert would be forced into the second open end as described in U.S. Pat. No. 5,387,192. For example, according to the present invention, the septum of U.S. Pat. No. 5,387,192 may be injection molded. Other methods of mechanical connection between the cup-shaped insert 130 and housing 120 could include threading the interior of lumen 127 of housing 120 and the exterior of the cup-shaped insert 130 for engagement between cup-shaped insert 130 and housing 120. Cup-shaped 130 insert could also be chemically bonded to housing 120, through the use of adhesives.

A disadvantage of using a cup-shaped insert which extends toward the septum is far field forces during the assembly process. Far field forces describe a substantial difference in location between where energy is applied and where force is exerted. For example, in the case of assembling a portal including a cup-shaped insert, when the cup-shaped insert is pushed into the housing the energy will be applied to the bottom of the insert but, the resultant force exerted by the insert against the housing is located at the top of the side wall of the insert.

Problems associated with far field forces may be significantly decreased if far field forces are turned into near field forces. Near field forces describe the situation when the resultant forces are close to the source of energy. Near field forces may be obtained by using a planar member to seal the second open end of the housing.

Figure 13:
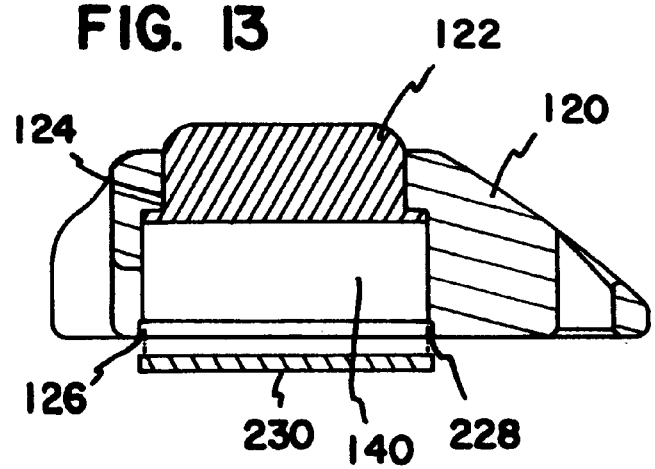
FIG. 13 is a cross-sectional exploded plan view of a partially assembled portal according to another preferred embodiment.
Figure 14:
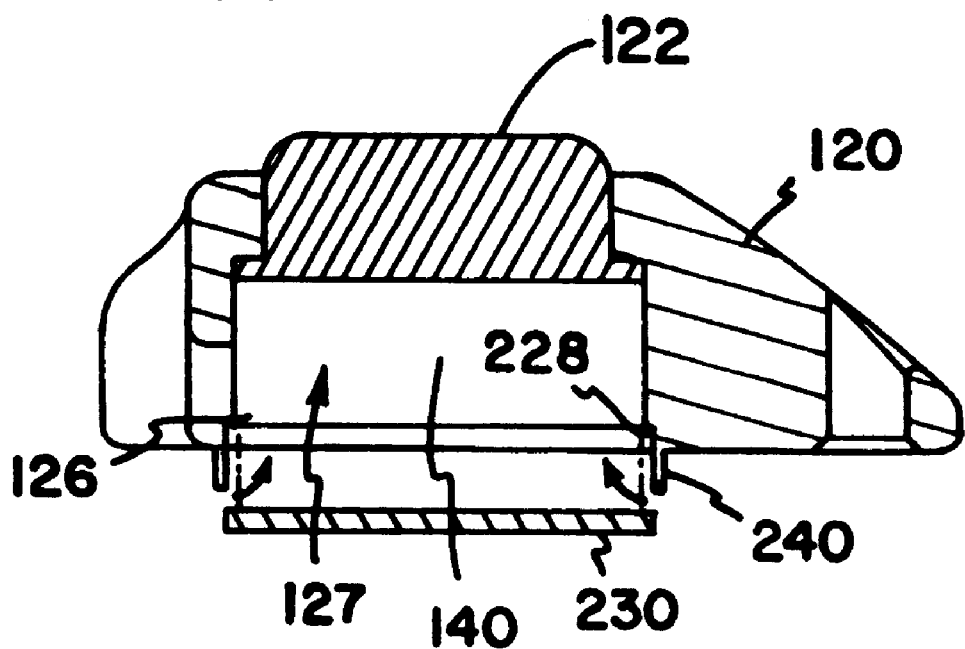
FIG. 14 is a cross-sectional exploded plan view of a partially assembled portal according to another preferred embodiment.

As illustrated in FIGS. 13 and 14, second open end 126 of housing 120 may be sealed with a planar member such as a disc 230. When using disc 230 to seal second open end 126, the energy-force relationship results in near field forces. In addition to disc 230 providing near field forces, significant expense is saved because disc 230 is constructed from a decreased volume of materials.

The prior art did not utilize discs to create sealed reservoirs because discs fail to provide sufficient force necessary to compress the septum. Disc 230 can be attached into second open end 126 in a variety of ways. These ways include ultrasonic welding, ultrasonic staking, screwing, snapping or bonding together with adhesives.

FIG. 13 shows a housing 120 having a septum 122 positioned in a first open end 124. Second open end 126 of housing 120 also includes a shelf 228. Shelf 228 operates to receive a disc 230. Disc 230 may be sealed onto shelf 228 through ultrasonic welding, snaps, threads, adhesives, or using other techniques known in the art.

As illustrated in FIG. 14, housing 220 may also include a plurality of flaps 240 which may be folded onto disc 230. Flaps 240 capture disc 230, and provide pressure between disc 230 and shelf 228.

Figure 15:
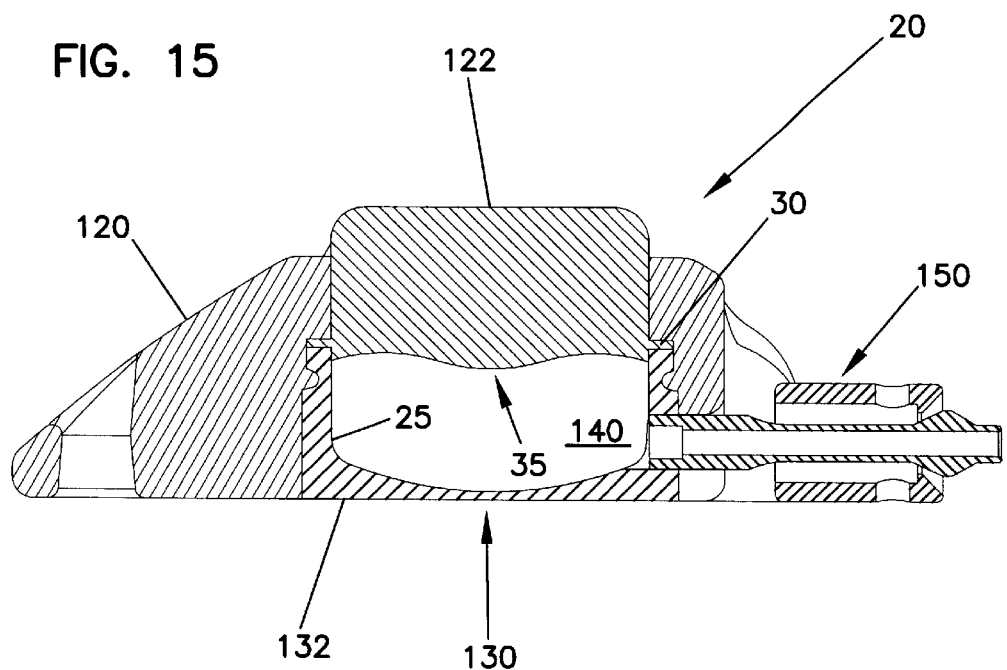
FIG. 15 is a cross-sectional plan view of a sealed portal according to another preferred embodiment.
Figure 16:
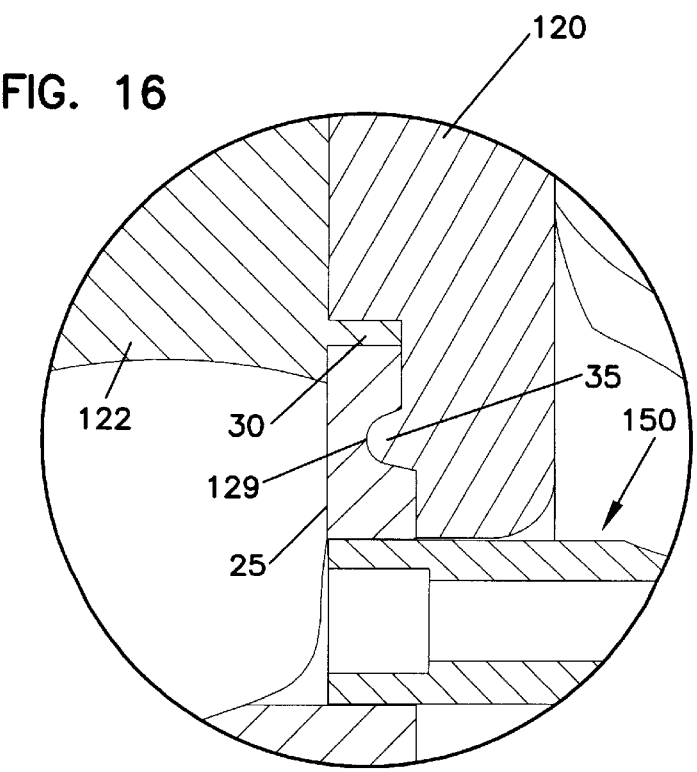
FIG. 16 is a fragmentary cross-sectional view of one region of the portal of FIG. 15.

Another preferred arrangement is illustrated in FIGS. 15 and 16. FIG. 15 is a cross-sectional view of the complete portal assembly. In this particular preferred arrangement, the associated height of insert 130 is great enough to contact septum 122 and squeeze a flanged region 30 of septum 122. The mechanical force of the squeeze on flanged region 30 by insert 130 is so great that it reduces the original width of flanged region 30 by about two-thirds. It is believed that the pressure on flanged region 30 by insert 130 is so great that it creates a wavy, or undulated surface 35 across a bottom of septum 122. It was discovered that this wavy surface 35 results in unexpected advantages. Specifically, it was discovered that the number of needle punctures sustained by septum 122 before leakage increased significantly. For example, in the embodiment illustrated in FIG. 11, insert 130 does not touch septum 122. In the FIG. 11 embodiment, the number of needle punctures before failure was about 1,200 to 1,500 sticks. It was discovered that in the FIG. 15 embodiment, by compressing flanged region 30 of septum 122 by insert 130, septum 122 can sustain up to 3,000 needle sticks before failure.

FIG. 16 illustrates in greater detail 130 compressing flanged region 30 of septum 122. Also illustrated in FIG. 16 is the portion 35 of housing 120 which is melted by ultrasonic staking solidified into annular ring 129 of insert 130. As explained above, this helps securely contain insert 130 into housing 120.

Septum 122 in the embodiments of FIGS. 15 and 16 is preferably injection molded into housing 120 in a non-compressive manner, as explained above. Prior to inserting cup-shaped insert 130, the bottom portion of septum 122 is flat and straight. That is, the wavy, or undulated, surface 35 of septum 122 is not created until insert 130 is compressed against flanged region 30. Septum 122 is non-compressively held in housing 120 because it is not compressed across the entire vertical dimension of septum 122. The compression on flanged region 30 by insert 130 is only across the vertical dimension of the flanged region 30, and not across the entire vertical dimension of septum 122.

It will be appreciated that the present invention may be used with any combination of plastic and metal. Specifically, the housing may be of plastic or metallic construction. As explained above, different adhesion enhancement techniques may be used with metallic and non-metallic metallic housings.

The present invention has significant advantages over the prior art. These advantages included decreased cost of manufacturing, increased puncture life and increased resistance to blowout. Further, because the septum is injection molded, design tolerances of manufacture may be greater also decreasing expense.

While the foregoing detailed description of the present invention describes the preferred embodiments, it will be appreciated that it is the intent of the inventors to include all modification and equivalent designs. Accordingly, the scope of the present invention is intended to be limited only by the claims which are appended hereto.

What is claimed is:

1. A portal for subcutaneous implantation comprising:
   a housing having a lumen accessible through a first open end; the lumen including an inner wall, the inner wall having an adhesion promoter thereon adjacent the first open end, said lumen having a longitudinal axis; and
   a cured in place elastomeric septum having an outer periphery bonded to the inner wall adjacent the first open end of the housing said septum cured in place by injection molding said septum into said open end, said septum having a vertical dimension in the direction of said longitudinal axis and being axially, non-compressively held within said lumen along at least a first portion of said vertical dimension.

2. The portal of claim 1, wherein the septum includes a bottom surface facing the lumen, the bottom surface being undulated in shape.

3. The portal of claim 1, wherein said septum is axially, non-compressively held along its entire vertical dimension.

4. The portal of claim 1, wherein the inner wall of the housing adjacent the first open end includes a roughened surface.

5. The portal of claim 1, wherein the inner wall of the housing adjacent the first open end includes a groove.

6. The portal of claim 1, wherein the septum is silicone and the adhesion promoter includes silane.

7. The portal of claim 1, wherein the housing further includes an outlet tube assembly operative in accessing the lumen.

8. The portal of claim 7, wherein the housing further includes a second open end opposite from the first open end; the second open end including an associated diameter; the portal further comprising a seal operative to close the second open end of the housing.

9. The portal of claim 8, wherein the seal comprises a cup-shaped insert.

10. The portal of claim 9, wherein the cup-shaped insert has an associated outer diameter larger than the associated diameter of the second open end of the housing, the cup-shaped inserted being forced into the second end of the housing to provide an interference fit between the housing and the cup-shaped insert.

11. The portal of claim 9, wherein the cup-shaped insert is ultrasonically staked to the housing.

12. The portal of claim 9, wherein the septum includes a flanged region along a second portion of said vertical dimension, and wherein the cup-shaped insert squeezably engages the flanged region.

13. The portal of claim 9, wherein the cup-shaped insert is spaced from the septum at a peripheral edge of the cup-shaped insert.

14. The portal of claim 8, wherein the seal is metallic.

15. The portal of claim 14, wherein the housing is metallic.

16. The portal of claim 8, wherein the seal is a planar.

17. The portal of claim 16, wherein the seal is a disc.

18. The portal of claim 17, wherein the disc is bonded to the housing adjacent the second end with adhesives.

19. The portal of claim 7, wherein the housing is non-metallic.

20. The portal of claim 19, wherein the housing is polysulfone.

21. A portal for subcutaneous implantation, the portal comprising:
   a housing having a first open end and a second end having a lumen therebetween, the lumen including an inner wall;
   an elastomeric septum positioned in the lumen of the housing against the inner wall adjacent the first open end of the housing, the septum having an outer periphery; and
   a planar member sealing the second end of the housing so as to define a sealed reservoir accessible through the septum, said planar member having a planar dimension not significantly larger than that of said second end, said planar member spaced from said outer periphery of said septum, wherein an air space is defined between said planar member and said outer periphery of said septum.

22. The portal of claim 21, wherein the housing further includes an outlet tube assembly operative in accessing the sealed reservoir.

23. The portal of claim 22, wherein the housing is ultransonically staked to the planar member.

24. The portal of claim 23, wherein the housing further includes an annular lip extending from the housing adjacent the second end, the lip folded over the planar member as to create a sealed reservoir.

25. The portal of claim 21, wherein the elastomeric septum is injection molded.

26. The portal of claim 21, wherein the planar member is a disc.

27. A portal for subcutaneous implantation comprising:

a housing having a first open end, and a lumen therebetween, a portion of the lumen having an adhesion promoter thereon adjacent the first open end;

a cured in place silicone septum sealing the first open end wherein the septum is injection molded into the first open end at the location of the adhesion promoter so as to be integrally formed with said lumen; and means for sealing the second open end.

28. The portal of claim 27, wherein the means for sealing includes a cup-shaped insert.

29. The portal of claim 27, wherein the means for sealing includes a disc.

30. The portal of claim 27, wherein the means for sealing forceably engages the septum.

31. The portal of claim 30, wherein the means for sealing includes a cup-shaped insert.

32. The portal of claim 27, wherein the septum has an undulated surface facing the lumen.

33. The portal of claim 27, wherein the septum includes a side surface, and the housing includes a groove adjacent to the side surface of the septum.

34. A portal for subcutaneous implantation comprising:

a silicone septum with first and second opposite surfaces, the second surface being undulated, the septum having a side surface;

an insert engaging the septum, the second surface of the septum facing the insert;

a housing holding the septum and the insert; and an adhesion promoter between the side surface of the septum and the housing, wherein the septum includes a flanged region and a non-flanged region along the side surface of the septum, and the insert forcibly squeezes the flanged region but not the non-flanged region, and wherein the septum is injection molded into the housing so as to be integrally formed with said lumen.

35. The portal of claim 34, wherein the insert includes an annular recess, and the housing is ultrasonically staked in to the recess.

36. The portal of claim 34, wherein the housing includes a groove adjacent to the side surface of the septum.

* * * * *